(12) United States Patent
Cohn et al.

(10) Patent No.: US 10,570,084 B2
(45) Date of Patent: Feb. 25, 2020

(54) GENERAL PURPOSE PLASTICIZERS BASED ON NAPHTHALIC ACID DIESTERS

(71) Applicant: ExxonMobil Research and Engineering Company, Annandale, NJ (US)

(72) Inventors: Stephen T. Cohn, Spring, TX (US); Christopher M. Evans, Kenmore, NY (US); Christine A. Costello, Easton, PA (US); James R. Lattner, LaPorte, TX (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 1 day.

(21) Appl. No.: 15/802,980

(22) Filed: Nov. 3, 2017

(65) Prior Publication Data

US 2018/0118660 A1   May 3, 2018

Related U.S. Application Data

(60) Provisional application No. 62/438,495, filed on Dec. 23, 2016, provisional application No. 62/416,944, filed on Nov. 3, 2016.

(51) Int. Cl.

| | |
|---|---|
| *C07C 67/08* | (2006.01) |
| *C07C 69/76* | (2006.01) |
| *C08K 5/00* | (2006.01) |
| *C07C 69/616* | (2006.01) |
| *C08K 5/12* | (2006.01) |
| *C07C 67/12* | (2006.01) |
| *C07C 69/753* | (2006.01) |
| *C07C 67/303* | (2006.01) |
| *C08F 14/06* | (2006.01) |
| *C08K 5/09* | (2006.01) |
| *C08L 75/04* | (2006.01) |
| *C08L 23/08* | (2006.01) |
| *C08L 27/06* | (2006.01) |
| *C08L 33/10* | (2006.01) |
| *C07D 307/92* | (2006.01) |
| *G01R 33/46* | (2006.01) |

(52) U.S. Cl.
CPC .............. *C07C 67/08* (2013.01); *C07C 67/12* (2013.01); *C07C 67/303* (2013.01); *C07C 69/616* (2013.01); *C07C 69/753* (2013.01); *C07C 69/76* (2013.01); *C08F 14/06* (2013.01); *C08K 5/0016* (2013.01); *C08K 5/09* (2013.01); *C08K 5/12* (2013.01); *C07C 2602/10* (2017.05); *C07C 2602/28* (2017.05); *C07D 307/92* (2013.01); *C08L 23/0853* (2013.01); *C08L 27/06* (2013.01); *C08L 33/10* (2013.01); *C08L 75/04* (2013.01); *G01R 33/46* (2013.01)

(58) Field of Classification Search
CPC ....... C07C 67/08; C07C 67/12; C07C 67/303; C07C 69/616; C07C 69/753; C07C 69/76; C07C 2602/10; C07C 2602/28; C08F 14/06; C08K 5/0016; C08K 5/09; C08K 5/12; C07D 307/92; C08L 23/0853; C08L 27/06; C08L 33/10; C08L 75/04
See application file for complete search history.

(56) References Cited

U.S. PATENT DOCUMENTS

| | | | |
|---|---|---|---|
| 1,909,092 A | | 5/1933 | Bruson |
| 2,233,513 A | | 3/1941 | Bruson |
| 2,372,947 A | | 4/1945 | Gresham |
| 2,512,675 A | | 6/1950 | Michel et al. |
| 3,110,724 A | | 11/1963 | Woodbridge et al. |
| 3,218,277 A | | 11/1965 | Ringwald et al. |
| 3,239,363 A | | 3/1966 | Burdge |
| 3,255,235 A | | 6/1966 | Coran et al. |
| 3,284,220 A | | 11/1966 | Anaguostopoulos et al. |
| 3,517,053 A | * | 6/1970 | Antonsen ................ C07C 67/03 560/80 |

(Continued)

FOREIGN PATENT DOCUMENTS

| | | |
|---|---|---|
| DE | 10146847 A1 | 4/2003 |
| EP | 0450621 A2 | 10/1991 |

(Continued)

OTHER PUBLICATIONS

CAS No. 1401986-54-6, STN CAS Registry, entered Oct. 24, 2012., 1 pg. (Year: 2012).*

(Continued)

*Primary Examiner* — Ana Z Muresan
(74) *Attorney, Agent, or Firm* — Kristina Okafor; Priya G. Prasad (57) ABSTRACT

A diester of a fused ring compound of the formula (I):

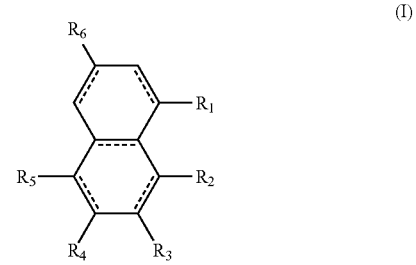

wherein: the fused rings are both aromatic; R1 and R4 to R6 substituents are H or ester moieties having C1 to C20 linear or branched alkyl chains; R2 and R3 are —C(O)OCxHy, wherein x is from 10 to 12 and y is from 21 to 25; two adjacent R1 to R4 substituents are —C(O)OCxHy, wherein x is from 10 to 12 and y is from 21 to 25; and when R3 and R4 are ester moieties, the alkyl chains of R4 are not C5 or C8; and polymer compositions containing the fused ring compound.

7 Claims, 2 Drawing Sheets

(56) References Cited

U.S. PATENT DOCUMENTS

| | | | |
|---|---|---|---|
| 3,624,133 | A | 11/1971 | Reitsema et al. |
| 3,719,466 | A * | 3/1973 | Ahle .................. A01C 1/06 47/57.6 |
| 3,772,389 | A | 11/1973 | Lowrance |
| 5,095,135 | A | 3/1992 | Yamada et al. |
| 6,274,756 | B1 | 8/2001 | Caers et al. |
| 6,482,972 | B1 | 11/2002 | Bahrmann et al. |
| 6,740,254 | B2 | 5/2004 | Zhou et al. |
| 6,777,514 | B2 | 8/2004 | Patil et al. |
| 7,297,738 | B2 | 11/2007 | Gosse et al. |
| 7,919,649 | B2 | 4/2011 | Compton et al. |
| 8,115,034 | B2 | 2/2012 | Godwin et al. |
| 8,476,350 | B2 | 7/2013 | Dakka et al. |
| 8,779,084 | B2 * | 7/2014 | Liu .................. C08G 63/672 528/272 |
| 8,859,821 | B2 | 10/2014 | Godwin et al. |
| 9,546,259 | B2 | 1/2017 | Colle et al. |
| 2002/0019559 | A1 | 2/2002 | Brunner et al. |
| 2006/0247461 | A1 | 11/2006 | Schlosberg et al. |
| 2009/0169775 | A1 | 7/2009 | Mukunoki et al. |
| 2014/0179845 | A1 | 6/2014 | Dakka et al. |

FOREIGN PATENT DOCUMENTS

| | | | |
|---|---|---|---|
| EP | 1182188 | * | 8/2001 |
| EP | 2465841 | A1 | 6/2012 |
| EP | 2965906 | * | 1/2016 |
| JP | 61126003 | A | 11/1984 |
| JP | H1129529 | * | 2/1999 |
| WO | 9932427 | A1 | 7/1999 |
| WO | 2003029339 | A1 | 9/2002 |
| WO | 2004046078 | A1 | 6/2004 |

OTHER PUBLICATIONS

English translation of JPH1129529, pp. 1-18 (Year: 1999).*
Asaoka et al., "Enantiodifferentiating Anti-Markovnikov Photoaddition of Alcohols to 1,1-Diphenylalkenes Sensitized by Chiral Naphthalenecarboxylates", J. Am. Chem. Soc. 1999, 121, 8486-8498. (Year: 1999).*
Adkins et al., "Selective Hydrogenation of Esters Containing a Naphthalene Nucleus", J. Am. Chem. Soc., 1949, vol. 71, pp. 3528-3531.
Burgess et al., "Chlorotris(triphenylphosphine)-rhodium(I)", Chem. Abstr. 2008, 149, 307083.
Cooke, "Formation of Polycyclic Carbocycles through Metal-Halogen Exchange-Initiated Intramolecular Conjugate Addition Reactions", J. Org. Chem., 1993, vol. 58, pp. 2910-2912.
Francis et al., "Highly Selective Adenosine A2 Receptor Agonists in a Series of N-Alkylated 2-Aminoadenosines", J. Med. Chem., 1991, vol. 34, pp. 2570-2579.
Godwyn, "Plasticizers", Applied Polymer Science 21st Century, ed. Craver and Carraher, Elsevier (2000), pp. 157-175.
Griebler et al., Combined Application of Stable Carbon Isotope Analysis and Specific Metabolites Determination for Assessing In Situ Degradation of Aromatic Hydrocarbons in a Tar Oil-Contaminated Aquifer., Environ. Sci. Technol., 2004, vol. 38, pp. 617-631.
Hagishita et al., "Optical Activity in βγ-Unsaturated Ketones. Part 2. Effect of the Magnitude and Energy of the Electric Transition Dipole Moment in the Aromatic Groups in 1- and 1,5 Substituted 9,10-Ethano-9,10-dihydroanthracen-11-one Derivatives.", J. Chem. Soc. Perkins Trans. 2, 1978, vol. 1, pp. 59-67.
Hunsberger et al., "The Determination of Double-bond Character in Cyclic Systems. IV. Tetrahydronaphthalene. Steric Facilitation of Chelation.", J. Am. Chem. Soc., 1958, vol. 80, pp. 3294-3300.
Konno et al., "Electrophilic Aromatic Substitution of Arenes with $CO_2$ Mediated by $R_3SiB(C_6F_5)_4$", Chem. Letters, 2012, vol. 41., pp. 913-914.
Markgraf et al., "The Diels-Alder Reaction of Methyl Propiolate With 1-Vinylcycloalkenes", Tetrahedron Letters, 1983, pp. 241-244, vol. 24, Issue 3.
Merle-Aubry et al., "Photophysics and Photochemistry of Naphthyl Ester Polymers in Solution", Macromolecules, 1980, vol. 13, pp. 1138-1143.
Nemoto et al., "Beneficial Effect of TMSCI in the Lewis Acid-mediated Carboxylation of Aromatic Compounds with Carbon Dioxide", Chemistry Letters, 2006, vol. 35. pp. 820-821.
Newman et al., "The Catalytic Dehydrogenation of 5-Substituted 1,2,3,4-Tetrahydronaphthalene Derivatives.", J. Am. Chem. Soc., 1952, vol. 74., pp. 905-908.
Suga et al., "Direct carboxylation of simple arenes with $CO_2$ through a rhodium-catalyzed C—H bond activation", Chemical Communications, 2014, vol. 50, pp. 14360-14363.
Yamada et al., "Asymmetric Acylations of sec-Alcohols with Twisted Amides Possessing Axial Chirality Induced by the Adjacent Asymmetric Center", J. Org. Chem., 1999, vol. 64, pp. 9365-9373.
Zezschwitz et al., "A One-Pot Sequence of Stille and Heck Couplings: Synthesis of Various 1,3,5-Hexatrienes and Their Subsequent 6-π-Electrocyclizations", Chem. Eur. J., 2001, vol. 7 No. 18, pp. 4035-4046.

* cited by examiner

GENERAL PURPOSE PLASTICIZERS BASED ON NAPHTHALIC ACID DIESTERS

CROSS-REFERENCE TO RELATED APPLICATIONS

This application claims the benefit of U.S. Provisional Application No. 62/416,944, filed on Nov. 3, 2016, the entire contents of which are incorporated herein by reference.

This application also claims the benefit of U.S. Provisional Application No. 62/438,495, filed on Dec. 23, 2016, the entire contents of which are incorporated herein by reference.

FIELD

Disclosed are diesters of fused ring compounds which find use as plasticizers for polymers.

BACKGROUND

Plasticizers are incorporated into a resin (usually a plastic or elastomer) to increase the flexibility, workability, or dispensability of the resin. The largest use of plasticizers is in the production of "plasticized" or flexible polyvinyl chloride (PVC) products. Typical uses of plasticized PVC include films, sheets, tubing, coated fabrics, wire and cable insulation and jacketing, toys, flooring materials such as vinyl sheet flooring or vinyl floor tiles, adhesives, sealants, inks, and medical products such as blood bags and tubing, and the like.

Other polymer systems that use small amounts of plasticizers include polyvinyl butyral, acrylic polymers, nylon, polyolefins, polyurethanes, and certain fluoroplastics. Plasticizers can also be used with rubber (although often these materials fall under the definition of extenders for rubber rather than plasticizers). A listing of the major plasticizers and their compatibilities with different polymer systems is provided in "Plasticizers," A. D. Godwin, in Applied Polymer Science 21st Century, edited by C. D. Craver and C. E. Carraher, Elsevier (2000); pp. 157-175.

Plasticizers can be characterized on the basis of their chemical structure. The most important chemical class of plasticizers is phthalic acid esters, which accounted for 85% worldwide of PVC plasticizer usage in 2002. However, in the recent past there has been an effort to decrease the use of phthalate esters as plasticizers in PVC, particularly in end uses where the product contacts food, such as bottle cap liners and sealants, medical and food films, or for medical examination gloves, blood bags, and IV delivery systems, flexible tubing, or for toys, and the like. For these and most other uses of plasticized polymer systems, however, a successful substitute for phthalate esters has heretofore not materialized.

One such suggested substitute for phthalates are esters based on cyclohexanoic acid. In the late 1990's and early 2000's, various compositions based on cyclohexanoate, cyclohexanedioates, and cyclohexanepolyoate esters were said to be useful for a range of goods from semi-rigid to highly flexible materials.

Other suggested substitutes include esters based on benzoic acid and polyketones. Epoxidized soybean oil, which has much longer alkyl groups ($C_{16}$ to $C_{18}$) has been tried as a plasticizer, but is generally used as a PVC stabilizer. Stabilizers are used in much lower concentrations than plasticizers. Additionally suggested are triglycerides with a total carbon number of the triester groups between 20 and 25, produced by esterification of glycerol with a combination of acids derived from the hydroformylation and subsequent oxidation of $C_3$ to $C_9$ olefins, having excellent compatibility with a wide variety of resins and that can be made with a high throughput.

However, additional plasticizers which have excellent compatibility with commonly plasticized polymers are still being sought to replace phthalate esters.

SUMMARY

In one form is presented a diester of a fused ring compound of the formula (I):

wherein the $R_1$ to $R_6$ substituents are H or ester moieties having $C_1$ to $C_{20}$ linear or branched alkyl chains, but when both fused rings are aromatic and $R_3$ and $R_4$ are ester moieties, the alkyl chains are not $C_5$ or $C_8$.

In another form, the fused rings of the diester are both aromatic, or only one of the fused rings is aromatic, or neither fused ring is aromatic.

Conveniently, two adjacent $R_1$ to $R_4$ substituents are ester moieties.

Advantageously, in this form the substituents $R_1$ and $R_2$ are —$C(O)OC_xH_y$, wherein x is from 3 to 12 and y is from 7 to 25, or the substituents $R_2$ and $R_3$ are —$C(O)OC_xH_y$, wherein x is from 3 to 12 and y is from 7 to 25, or the substituents $R_3$ and $R_4$ are —$C(O)OC_xH_y$, wherein x is from 3 to 12 and y is from 7 to 25, or wherein $R_2$ and $R_5$ are —$C(O)OC_xH_y$, wherein x is from 3 to 12 and y is from 7 to 25, or wherein $R_3$ and $R_6$ are —$C(O)OC_xH_y$, wherein x is from 3 to 12 and y is from 7 to 25, except that when both fused rings are aromatic, x is not 5 or 8.

In another form is presented a diester of a fused ring compound of the formula (II):

wherein the $R_1$ to $R_6$ substituents are H or ester moieties having $C_1$ to $C_{20}$ linear or branched alkyl chains.

Conveniently, two adjacent $R_1$ to $R_4$ substituents are ester moieties.

Advantageously, in this form the substituents $R_1$ and $R_2$ are —C(O)OC$_x$H$_y$, wherein x is from 3 to 12 and y is from 7 to 25, or the substituents $R_2$ and $R_3$ are —C(O)OC$_x$H$_y$, wherein x is from 3 to 12 and y is from 7 to 25, or the substituents $R_3$ and $R_4$ are —C(O)OC$_x$H$_y$, wherein x is from 3 to 12 and y is from 7 to 25, or wherein $R_2$ and $R_5$ are —C(O)OC$_x$H$_y$, wherein x is from 3 to 12 and y is from 7 to 25, or wherein $R_3$ and $R_6$ are —C(O)OC$_x$H$_y$, wherein x is from 3 to 12 and y is from 7 to 25.

In another form is presented a diester of a fused ring compound of the formula (III):

(III)

wherein the $R_1$ to $R_6$ substituents are H or ester moieties having $C_1$ to $C_{20}$ linear or branched alkyl chains.

Conveniently, two adjacent $R_1$ to $R_4$ substituents are ester moieties.

Advantageously, in this form the substituents $R_1$ and $R_2$ are —C(O)OC$_x$H$_y$, wherein x is from 3 to 12 and y is from 7 to 25, or the substituents $R_2$ and $R_3$ are —C(O)OC$_x$H$_y$, wherein x is from 3 to 12 and y is from 7 to 25, or the substituents $R_3$ and $R_4$ are

—C(O)OC$_x$H$_y$, wherein x is from 3 to 12 and y is from 7 to 25, or wherein $R_2$ and $R_5$ are —C(O)OC$_x$H$_y$, wherein x is from 3 to 12 and y is from 7 to 25, or wherein $R_3$ and $R_6$ are

—C(O)OC$_x$H$_y$, wherein x is from 3 to 12 and y is from 7 to 25.

In another form is presented a method of making a naphthalic acid based diester having adjacent ester substituents, comprising:

supplying a di-substituted naphthalene of the formula:

oxidizing the di-substituted naphthalene to form an anhydride intermediate of the formula:

and esterifying the anhydride intermediate with an alcohol, ROH, wherein R is a $C_1$ to $C_{20}$ linear or branched alkyl group, to form adjacent napthalic diesters of the formula:

Advantageously, the method can further comprise hydrogenating at least one of the fused rings to form diesters of the formula:

In another form is presented a polymer composition comprising a thermoplastic polymer and at least one plasticizer of the formula (I):

(I)

wherein the $R_1$ to $R_6$ substituents are H or ester moieties having $C_1$ to $C_{20}$ linear or branched alkyl chains, but when both fused rings are aromatic and $R_3$ and $R_4$ are ester moieties, the alkyl chains are not $C_5$ or $C_8$.

Advantageously, the thermoplastic polymer is selected from the group consisting of vinyl chloride resins, polyesters, polyurethanes, ethylene-vinyl acetate copolymer, rubbers, poly(meth)acrylics and combinations thereof.

DETAILED DESCRIPTION

All numerical values within the detailed description and the claims herein are modified by "about" or "approximately" the indicated value, and take into account experimental error and variations that would be expected by a person having ordinary skill in the art.

There is an increased interest in developing new plasticizers that are non-phthalates and which possess good plasticizer performance characteristics but are still competitive economically. The present disclosure is directed towards non-phthalate ester plasticizers, particularly OXO-ester plasticizers, that can be made from low cost feeds and employ fewer manufacturing steps in order to meet economic targets.

Definitions

An "OXO-ester" is a compound having at least one functional ester moiety within its structure derived from esterification of either an acid or alcohol compound with an OXO-alcohol or OXO-acid, respectively.

An "OXO-alcohol" is an organic alcohol, or mixture of organic alcohols, which is prepared by hydroformylating an olefin, followed by hydrogenation to form the alcohols. Typically, the olefin is formed by light olefin oligomerization over heterogenous acid catalysts, which olefins are readily available from refinery processing operations. The reaction results in mixtures of longer-chain, branched olefins, which subsequently form longer chain, branched alcohols, as described in U.S. Pat. No. 6,274,756, incorporated herein by reference in its entirety. The OXO-alcohols consist of multiple isomers of a given chain length due to the various isomeric olefins obtained in the oligomerization process, in tandem with the multiple isomeric possibilities of the hydroformylation step.

An "OXO-acid" is an organic acid, or mixture of organic acids, which is prepared by hydroformylating an olefin, followed by oxidation to form the acids. Typically, the olefin is formed by light olefin oligomerization over heterogenous acid catalysts, which olefins are readily available from refinery processing operations. The reaction results in mixtures of longer-chain, branched olefins, which subsequently form longer-chain, branched acids. The OXO-acids similarly consist of multiple isomers of a given chain length.

The purpose of the presently disclosed plasticizers is to replace the currently used, phthalate-based plasticizers with a non-phthalate alternative for the global general purpose plasticizer market. Esters of naphthalic acid are described and tested as general purpose plasticizers with properties rivaling commercially used DINP (diisononyl phthalate). The molecules presented are non-phthalates, yet show performance comparable to the currently deployed commercial technology. These plasticizers utilize di-esters of naphthalene as the base architecture for the plasticizer which offer good physical properties such as miscibility with PVC, clarity, non-volatility and low viscosity.

The structures and positional numbering of the naphthalene-based plasticizers is shown below.

$R_1$ = any alkyl ($C_1$ or $C_{20}$)  substitution nomenclature

The ester substitutions can be located at any two positions on the rings, such as at the 1,4- or 2,6-positions, but adjacent positions are advantageous (e.g. 1,2-; 1,8-; 2,3-) with the 1,8-substitution being most advantageous. The core can be (N) naphthalene-based, partially hydrogenated to a tetralin-like core (T), or fully-hydrogenated to a decalin-like structure (D). Further, the ester functionality can be made from any alcohol from $C_1$ to $C_{20}$. The general structure of a 1,8-naphthalene diester is shown below:

Advantageously, the low volatility of these naphthalene-based structures allows for the use of shorter-chain alcohols, such as isopropyl alcohol, to form the ester moiety. It has been found that shorter alcohol chains on these naphthalene-based structures actually result in more viscous materials.

A preferred starting structure for the presently disclosed plasticizers is a di-methyl substituted naphthalene, which methyl groups are subsequently oxidized to form carboxylic acid substituents. It is advantageous if the methyl substituents are located at adjacent positions on the naphthalene core. The potential dimethyl naphthalenes useful for forming the naphthalene diester plasticizers of the present application are shown below, which are the 1,2-, 2,3- and 1,8-dimethyl substituted naphthalenes respectively.

The oxidation process of making the esters is less-complex and more cost-effective if the hydrocarbon feed proceeds through an anhydride intermediate rather than having to complete two sequential oxidations.

The multiple oxidation process is more difficult and requires special processing. As an example, the oxidation of para-xylene is more challenging than ortho-xylene for the same reason.

Further, the 1,8-diester substitution is interesting because each functionality is located on a different ring via a peri-substitution, which may significantly affect the toxicological behavior relative to phthalate-like ortho-type substitutions. Likewise, the 2,6-diester substitution has each functionality on different rings.

An additional variation on this family of molecules is related to the aromatic core. The original naphthalene-based ester (N) can be hydrogenated such that only one ring becomes saturated (T) or both rings are saturated (D), so that all aromaticity is removed. Analogously to the change in performance observed in going from DINP to 1,2-cyclohexane dicarboxylic acid diisononyl esters (DINCH), ring hydrogenation improves toxicology and allows for tuning of plasticizer performance.

N

Y

D

For example, the diesters of the present application can be those of the formula (I) below:

(I)

wherein the $R_1$ to $R_6$ substituents are H or ester moieties having $C_1$ to $C_{20}$ linear or branched alkyl chains, but when both fused rings are aromatic and $R_3$ and $R_4$ are ester moieties, the alkyl chains are not $C_5$ or $C_8$. The diesters of formula (I) can be those wherein both rings are aromatic rings, such as naphthalene.

Alternatively, the diesters can be those of formula (II) below:

(II)

wherein the $R_1$ to $R_6$ substituents are H or ester moieties having $C_1$ to $C_{20}$ linear or branched alkyl chains.

In another form, the diesters of the present application can be those of formula (III) below:

(III)

wherein the $R_1$ to $R_6$ substituents are H or ester moieties having $C_1$ to $C_{20}$ linear or branched alkyl chains.

Advantageously, the alkyl chains can be $C_1$ to $C_{20}$ alkyl chains, or even $C_3$ to $C_{18}$ alkyl chains, or even $C_3$ to $C_{12}$ alkyl chains. In all instances, the alkyl chains can be linear or branched alkyls. The ester moieties are formed by reacting the carboxylic acid substituents on the rings with linear or branched alcohols, such as OXO-alcohols, under esterification conditions.

In one form, $R_1$ and $R_2$ are —C(O)OC$_x$H$_y$, wherein x is from 3 to 12 and y is from 7 to 25, or $R_2$ and $R_3$ are —C(O)OC$_x$H$_y$, wherein x is from 3 to 12 and y is from 7 to 25, or $R_3$ and $R_4$ are —C(O)OC$_x$H$_y$, wherein x is from 3 to 12 and y is from 7 to 25, or wherein $R_2$ and $R_5$ are —C(O)OC$_x$H$_y$, wherein x is from 3 to 12 and y is from 7 to 25, or wherein $R_3$ and $R_6$ are —C(O)OC$_x$H$_y$, wherein x is from 3 to 12 and y is from 7 to 25, except when both fused rings are aromatic, x is not 5 or 8. It can be advantageous if two adjacent $R_1$ to $R_4$ substituents are ester moieties.

In another form the present application discloses a method of making a naphthalic acid based diester having adjacent ester substituents, comprising supplying a di-substituted naphthalene of the formula:

oxidizing the di-substituted naphthalene over a catalyst to form an anhydride intermediate of the formula:

and
esterifying the anhydride intermediate with an alcohol, ROH, wherein R is a $C_1$ to $C_{20}$ linear or branched alkyl group, to form adjacent napthalic diesters of the formula:

In another form, 1,8-naphthalic anhydride can be prepared by oxidizing acenaphthene or acenaphthylene, which occur naturally in coal tar, as follows:

The method can further comprise hydrogenating at least one of the fused rings to form diesters of the formula:

In another form the application is directed to a polymer composition comprising a thermoplastic polymer and at least one plasticizer of the formula (I):

wherein the $R_1$ to $R_6$ substituents are H or ester moieties having $C_1$ to $C_{20}$ linear or branched alkyl chains, but when both fused rings are aromatic and $R_3$ and $R_4$ are ester moieties, the alkyl chains are not $C_5$ or $C_8$. Suitable thermoplastic polymers include vinyl chloride resins, polyesters, polyurethanes, ethylene-vinyl acetate copolymer, rubbers, poly(meth)acrylics and combinations thereof.

EXAMPLES

Example 1: Preparation of
1,8-Naphthalenedicarboxylic Acid, Didecyl Ester

A 1000-mL 3-neck round bottom fitted with a Dean-Stark apparatus was charged with 1,8-naphthalic anhydride (10.0 g, 50.46 mmol), 1-decanol (300 mL, 1571 mmol), xylenes (200 mL), and p-toluenesulfonic acid monohydrate (0.96 g, 5.05 mmol). The solution was refluxed under a dry nitrogen atmosphere for 48 h after which only a trace of anhydride was detected by TLC (20% EtOAc/hexanes). The reaction was concentrated under high vacuum (<1 Torr) to 27.73 g crude product as an amber colored oil that was ~85% pure by GC (approx. 94% yield). Impurities identified by $^1$H NMR were didecyl ether (major) and decyl p-toluenesulfonate. The crude material was combined with other preparations and purified by automated column chromatography (2x) in 3-5 g batches producing approximately 1.5-3 g of purified material (99+% by $^1$H NMR) each run as a light yellow oil (Biotage, 100 g SNAP ultra, 0-5% EtOAc/hexanes). To further reduce color the accumulated purified product (23.5 g) was dissolved in hexane (200 mL), stirred with decolorizing carbon (2 g) for 2 h, filtered through a silica gel plug, and concentrated under high vacuum (<1 Torr) at 105° C. for 2 h to remove all volatiles.

The 1,8-naphthalenedicarboxylic acid, didecyl ester was blended into PVC and tested in several primary screens (viscosity, volatility, flex onset, thermal stability and efficiency). The viscosity, volatility and thermal stability of this complex was measured to be better than the industry standard (DOP and DINP). The Table below compares the viscosities of various commercially available plasticizers and of the Example 1 plasticizer.

| Plasticizer | Viscosity @ 334.4 sec$^{-1}$ |
|---|---|
| Diisononylphthalate (DINP) | 81.3 |
| Diisononylcyclohexane (DINCH) | 50.5 |
| Dioctylphthalate (DOP) | 86 |
| 1,8-naphthalenedicarboxylic acid, didecyl ester (Ex. 1) | 75.1 |

Figure 1:
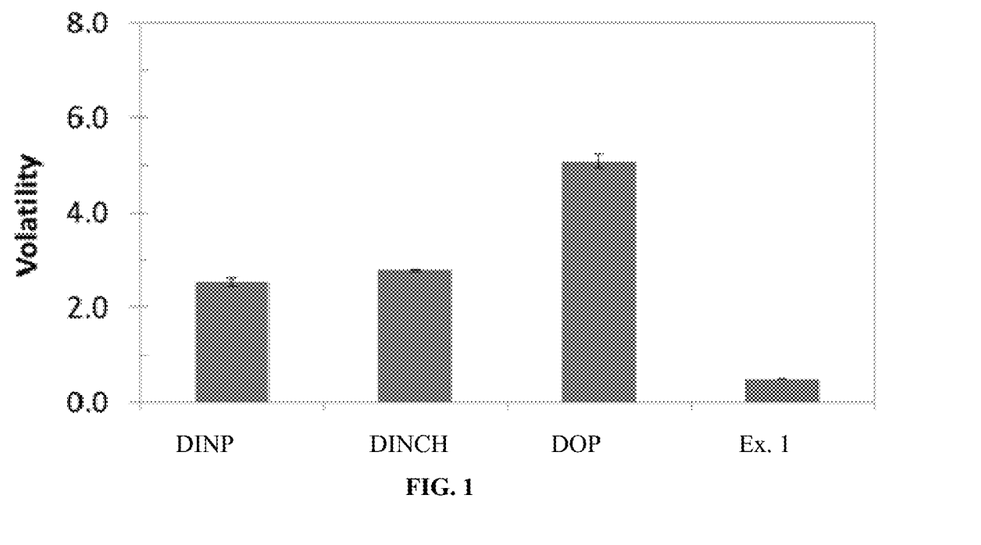
FIG. 1 is a graph showing the relative volatility of commercial plasticizers and the compound of Example 1.

FIG. 1 is a graph showing the relative volatility of the commercial plasticizers and the compound of Example 1. The larger-sized core of Example 1 ($C_{10}$) compared to the commercial plasticizers ($C_6$) is likely the reason for the significant reduction in volatility. This is a very important feature in commercial applications and the very low value for 1,8-naphthalenedicarboxylic acid, didecyl ester permits optimizing structural changes, such as use of shorter side-chains to improve other properties while maintaining an attractive low volatility. For example, butyl or isopropyl alcohols are too short for the conventional phthalate-based plasticizers but the low volatility of 1,8-naphthalenedicarboxylic acid, didecyl ester allows for significant give-away and should allow the use of cheaper alcohol feedstocks.

In accelerated thermal testing the blended Example 1/PVC bars did not exhibit any exudation during testing. This implies that the Example 1 plasticizer has good miscibility with PVC and does not phase segregate. Further, it was found that that the molecule does not thermally decompose (i.e. 50 wt. % loss) until 279° C.; as compared to 299° C. for DINP.

Figure 2:
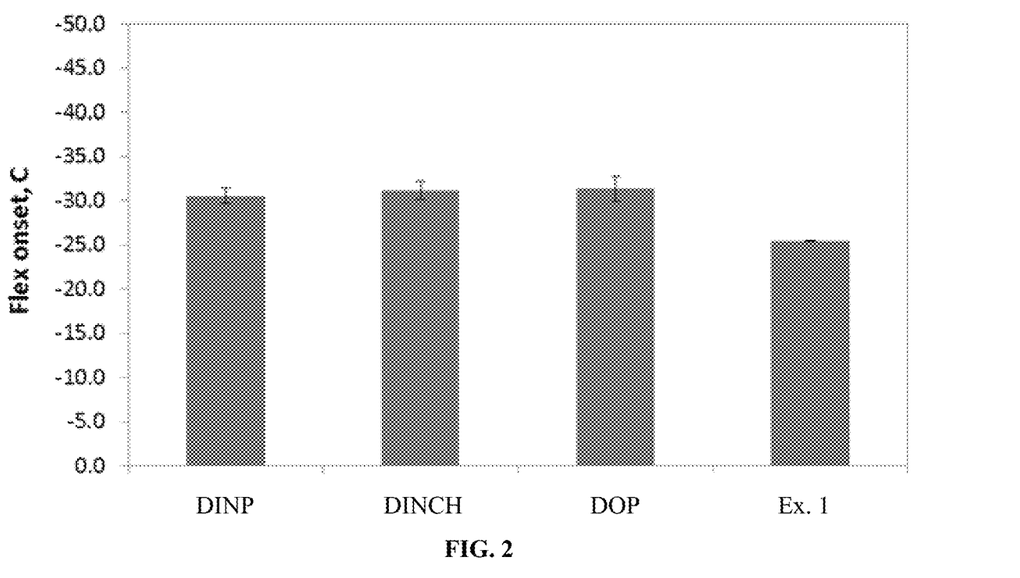
FIG. 2 is a graph displaying the flex onset for PVC blends made using the listed plasticizers.

FIG. 2 is a graph displaying the flex onset for PVC blends made using the listed plasticizers. The flex onset is a measure of the low temperature performance of the PVC blends. A lower value is better as the blends can be used in colder applications without any degradation of product performance. The Example 1 plasticizer slightly under performs the commercial controls, but optimization with other alcohols, such as OXO-alcohols, could achieve better low temperature flex.

Figure 3:
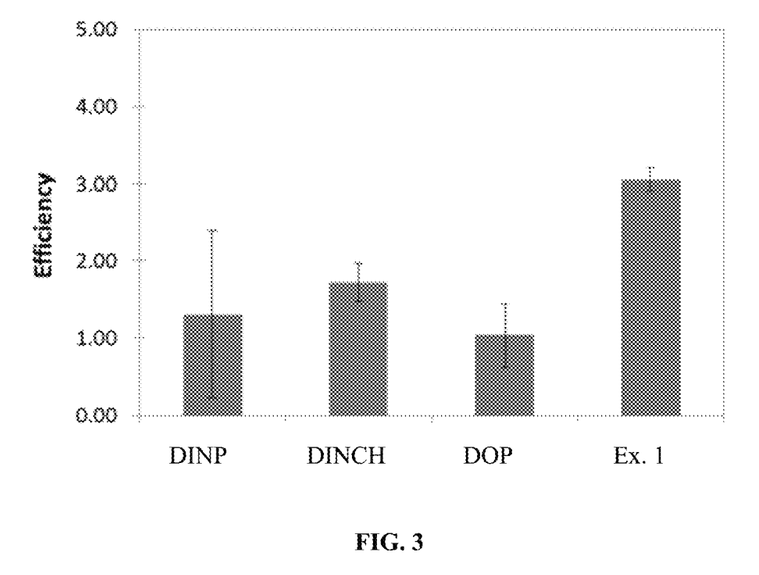
FIG. 3 is a graph displaying the relative efficiency of the tested plasticizers in PVC blends.

FIG. 3 is a graph displaying the relative efficiency of the tested plasticizers in PVC blends. The efficiency is a relative measure of how much material is required to achieve a flexible PVC blend. The efficiency of DOP is set as 1.0.

PCT/EP Clauses

1. A diester of a fused ring compound of the formula (I):

(I)

wherein the $R_1$ to $R_6$ substituents are H or ester moieties having $C_1$ to $C_{20}$ linear or branched alkyl chains, but when both fused rings are aromatic and $R_3$ and $R_4$ are ester moieties, the alkyl chains are not $C_5$ or $C_8$.

2. The diester of clause 1, wherein the fused rings are both aromatic, or wherein only one of the fused rings is aromatic, or wherein neither fused ring is aromatic.

3. The diester of either one of clauses 1 or 2, wherein $R_1$ and $R_2$ are —C(O)OC$_x$H$_y$, wherein x is from 3 to 12 and y is from 7 to 25, or wherein $R_2$ and $R_3$ are —C(O)OC$_x$H$_y$, wherein x is from 3 to 12 and y is from 7 to 25, or wherein $R_3$ and $R_4$ are

—C(O)OC$_x$H$_y$, wherein x is from 3 to 12 and y is from 7 to 25, or wherein $R_2$ and $R_5$ are —C(O)OC$_x$H$_y$, wherein x is from 3 to 12 and y is from 7 to 25, or wherein $R_3$ and $R_6$ are —C(O)OC$_x$H$_y$, wherein x is from 3 to 12 and y is from 7 to 25, except that when both fused rings are aromatic, x is not 5 or 8.

4. The diester of any one of clauses 1 to 3, wherein two adjacent $R_1$ to $R_4$ substituents are said ester moieties.

5. A diester of a fused ring compound of the formula (II):

(II)

wherein the $R_1$ to $R_6$ substituents are H or ester moieties having $C_1$ to $C_{20}$ linear or branched alkyl chains.

6. The diester of clause 5, wherein $R_1$ and $R_2$ are —C(O)OC$_x$H$_y$, wherein x is from 3 to 12 and y is from 7 to 25, or wherein $R_2$ and $R_3$ are —C(O)OC$_x$H$_y$, wherein x is from 3 to 12 and y is from 7 to 25, or wherein $R_3$ and $R_4$ are

—C(O)OC$_x$H$_y$, wherein x is from 3 to 12 and y is from 7 to 25, or wherein $R_2$ and $R_5$ are —C(O)OC$_x$H$_y$, wherein x is from 3 to 12 and y is from 7 to 25, or wherein $R_3$ and $R_6$ are —C(O)OC$_x$H$_y$, wherein x is from 3 to 12 and y is from 7 to 25.

7. The diester of either of clauses 5 or 6, wherein two adjacent $R_1$ to $R_4$ substituents are said ester moieties.

8. A diester of a fused ring compound of the formula (III):

(III)

wherein the $R_1$ to $R_6$ substituents are H or ester moieties having $C_1$ to $C_{20}$ linear or branched alkyl chains.

9. The diester of clause 8, wherein $R_1$ and $R_2$ are —C(O)OC$_x$H$_y$, wherein x is from 3 to 12 and y is from 7 to 25, or wherein $R_2$ and $R_3$ are —C(O)OC$_x$H$_y$, wherein x is from 3 to 12 and y is from 7 to 25, or wherein $R_3$ and $R_4$ are —C(O)OC$_x$H$_y$, wherein x is from 3 to 12 and y is from 7 to 25, or wherein $R_2$ and $R_5$ are

—C(O)OC$_x$H$_y$, wherein x is from 3 to 12 and y is from 7 to 25, or wherein $R_3$ and $R_6$ are —C(O)OC$_x$H$_y$, wherein x is from 3 to 12 and y is from 7 to 25.

10. The diester of either of clauses 8 or 9, wherein two adjacent $R_1$ to $R_4$ substituents are said ester moieties.

11. A method of making a naphthalic acid based diester having adjacent ester substituents, comprising:

supplying a di-substituted naphthalene of the formula:

oxidizing the di-substituted naphthalene to form an anhydride intermediate of the formula:

and esterifying the anhydride intermediate with an alcohol, ROH, wherein R is a $C_1$ to $C_{20}$ linear or branched alkyl group, to form adjacent napthalic diesters of the formula:

12. The method of clause 11, further comprising hydrogenating at least one of the fused rings to form diesters of the formula:

13. A polymer composition comprising a thermoplastic polymer and at least one plasticizer of the formula (I):

wherein the $R_1$ to $R_6$ substituents are H or ester moieties having $C_1$ to $C_{20}$ linear or branched alkyl chains, but when both fused rings are aromatic and $R_3$ and $R_4$ are ester moieties, the alkyl chains are not $C_5$ or $C_8$.

14. The polymer composition of clause 13, wherein the thermoplastic polymer is selected from the group consisting of vinyl chloride resins, polyesters, polyurethanes, ethylene-vinyl acetate copolymer, rubbers, poly(meth)acrylics and combinations thereof.

INDUSTRIAL APPLICABILITY

The systems and methods disclosed herein are applicable to the polymer industry. It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

The invention claimed is:

1. A diester of a fused ring compound of the formula (I):

(I)

wherein:
the fused rings are both aromatic;
$R_1$ and $R_4$ to $R_6$ substituents are H or ester moieties having $C_1$ to $C_{20}$ linear or branched alkyl chains; R2 and R3 are —C(O)OCxHy, wherein x is from 10 to 12 and y is from 21 to 25;
two adjacent $R_1$ to $R_4$ substituents are —C(O)OC$_x$H$_y$, wherein x is from 10 to 12 and y is from 21 to 25; and
when $R_3$ and $R_4$ are ester moieties, the alkyl chains of R4 are not $C_5$ or $C_8$.

2. The diester of claim 1, wherein $R_1$ is —C(O)OC$_x$H$_y$, wherein x is from 10 to 12 and y is from 21 to 25.

3. The diester of claim 1, wherein $R_2$ and $R_5$ are —C(O)OC$_x$H$_y$, wherein x is from 3 to 12 and y is from 7 to 25.

4. The diester of claim 1, wherein is —C(O)OC$_x$H$_y$, wherein x is from 3 to 12 and y is from 7 to 25.

5. A method of making a naphthalic acid based diester having adjacent ester substituents, comprising:
supplying a di-substituted naphthalene of the formula:

oxidizing the di-substituted naphthalene to form an anhydride intermediate of the formula:

, or and
esterifying the anhydride intermediate with an alcohol, ROH, wherein R is a $C_1$ to $C_{20}$ linear or branched alkyl group, to form adjacent napthalic diesters of the formula:

6. The method of claim 5, further comprising hydrogenating at least one of the fused rings to form diesters of the formula:

-continued

7. A polymer composition comprising a thermoplastic polymer and at least one diester of a fused ring compound of claim 1, wherein the thermoplastic polymer is selected from the group consisting of vinyl chloride resins, polyesters, polyurethanes, ethylene-vinyl acetate copolymer, rubbers, and poly(meth)acrylics.

* * * * *